US009737720B2

(12) United States Patent
Meyer

(10) Patent No.: US 9,737,720 B2
(45) Date of Patent: Aug. 22, 2017

(54) CARDIAC PACEMAKER AND USES THEREOF

(71) Applicant: The University of Vermont and State Agricultural College, Burlington, VT (US)

(72) Inventor: Markus Meyer, Williston, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 0 days.

(21) Appl. No.: 15/212,708

(22) Filed: Jul. 18, 2016

(65) Prior Publication Data
US 2016/0325103 A1 Nov. 10, 2016

Related U.S. Application Data

(63) Continuation of application No. 14/387,971, filed as application No. PCT/US2013/030752 on Mar. 13, 2013, now Pat. No. 9,403,016.

(60) Provisional application No. 61/616,162, filed on Mar. 27, 2012.

(51) Int. Cl.
*A61N 1/36* (2006.01)
*A61N 1/365* (2006.01)

(52) U.S. Cl.
CPC ......... *A61N 1/36585* (2013.01); *A61N 1/365* (2013.01); *A61N 1/36514* (2013.01); *A61N 1/36535* (2013.01); *A61N 1/36542* (2013.01); *A61N 1/36507* (2013.01)

(58) Field of Classification Search
CPC ... A61N 1/36592; A61N 1/365; A61N 1/3627

USPC .......................................................... 607/6–9
See application file for complete search history.

(56) References Cited

U.S. PATENT DOCUMENTS

| | | |
|---|---|---|
| 3,885,552 A | 5/1975 | Kennedy |
| 4,567,892 A | 2/1986 | Plicchi et al. |
| 4,644,954 A | 2/1987 | Wittkampf et al. |
| 4,688,573 A | 8/1987 | Alt |
| 4,721,110 A | 1/1988 | Lampadius |
| 4,803,987 A | 2/1989 | Calfee et al. |
| 4,867,161 A | 9/1989 | Schaldach |
| 4,884,576 A | 12/1989 | Alt |
| 5,097,831 A | 3/1992 | Lekholm |
| 5,197,467 A | 3/1993 | Steinhaus et al. |
| 5,292,340 A | 3/1994 | Crosby et al. |

(Continued)

FOREIGN PATENT DOCUMENTS

| | | |
|---|---|---|
| DE | 2346223 A1 | 3/1975 |
| EP | 0242510 A2 | 10/1987 |
| WO | WO 97/43001 A1 | 11/1997 |

OTHER PUBLICATIONS

International Search Report and Written Opinion for International Application No. PCT/US2013/030752 mailed May 22, 2013.

(Continued)

*Primary Examiner* — Paula J Stice
(74) *Attorney, Agent, or Firm* — Wolf, Greenfield & Sacks, P.C.

(57) ABSTRACT

The invention relates to improved cardiac pacemakers and methods of use thereof. In particular the cardiac pacemakers are useful for normalizing heart rates over resting heart rates in order to condition the heart to improve overall cardiac output.

9 Claims, 2 Drawing Sheets

(56) References Cited

U.S. PATENT DOCUMENTS

| | | | |
|---|---|---|---|
| 5,318,597 A | 6/1994 | Hauck et al. | |
| 5,467,773 A | 11/1995 | Bergelson et al. | |
| 5,645,576 A | 7/1997 | Limousin et al. | |
| 5,694,940 A | 12/1997 | Unger et al. | |
| 5,733,312 A * | 3/1998 | Schloss | A61N 1/36585 607/17 |
| 5,861,011 A | 1/1999 | Stoop | |
| 5,876,353 A | 3/1999 | Riff | |
| 5,919,141 A | 7/1999 | Money et al. | |
| 6,485,416 B1 | 11/2002 | Platt et al. | |
| 6,975,903 B1 | 12/2005 | Min et al. | |
| 7,133,718 B2 | 11/2006 | Bakken | |
| 8,126,549 B2 | 2/2012 | Sigg et al. | |
| 9,403,016 B2 * | 8/2016 | Meyer | A61N 1/36514 |
| 2001/0012954 A1 | 8/2001 | Czygan et al. | |
| 2001/0023360 A1 | 9/2001 | Nelson et al. | |
| 2001/0056229 A1 | 12/2001 | Cosentino et al. | |
| 2002/0095093 A1 | 7/2002 | Au et al. | |
| 2002/0143263 A1 | 10/2002 | Shusterman | |
| 2003/0153955 A1* | 8/2003 | Park | A61N 1/365 607/17 |
| 2004/0260348 A1* | 12/2004 | Bakken | A61N 1/365 607/9 |
| 2005/0251218 A1* | 11/2005 | Markowitz | A61N 1/3601 607/17 |
| 2006/0047205 A1 | 3/2006 | Ludomirsky et al. | |
| 2006/0074465 A1 | 4/2006 | Webb | |
| 2006/0211934 A1 | 9/2006 | Hassonjee et al. | |
| 2007/0027371 A1 | 2/2007 | Benaron et al. | |
| 2007/0282177 A1 | 12/2007 | Pilz | |
| 2008/0114408 A1 | 5/2008 | Shuros et al. | |
| 2008/0269573 A1 | 10/2008 | Najafi et al. | |
| 2009/0234401 A1 | 9/2009 | Zielinski et al. | |
| 2010/0057157 A1 | 3/2010 | Govari et al. | |
| 2010/0082077 A1 | 4/2010 | Bruns | |
| 2011/0273309 A1 | 11/2011 | Zhang et al. | |
| 2012/0010674 A1 | 1/2012 | Pastore et al. | |
| 2012/0041502 A1 | 2/2012 | Schwartz et al. | |
| 2012/0046528 A1 | 2/2012 | Eigler et al. | |

OTHER PUBLICATIONS

International Preliminary Report on Patentability for International Application No. PCT/US2013/030752 mailed Oct. 9, 2014.

Kass et al., The restoration of chronotropic competence in heart failure patients with normal ejection fraction (RESET) study: rationale and design. J Card Fail. Jan. 2010;16(1):17-24. doi: 10.1016/j.cardfail.2009.08.008. Epub Oct. 7, 2009.

* cited by examiner

CARDIAC PACEMAKER AND USES THEREOF

RELATED APPLICATIONS

This application is a continuation of U.S. application Ser. No. 14/387,971, filed Sep. 25, 2014, which is a national stage filing under U.S.C. §371 of PCT International Application PCT/US2013/030752, filed Mar. 13, 2013, which claims priority under 35 U.S.C. §119(e) to U.S. Provisional Application Ser. No. 61/616,162, entitled "CARDIAC PACEMAKER AND USES THEREOF," filed on Mar. 27, 2012, which applications are herein incorporated by reference in their entireties.

FIELD OF THE INVENTION

Improved cardiac pacemakers and methods of use thereof are described. In particular the cardiac pacemakers are useful for increasing heart rates over resting heart rates in order to condition the heart and increase the chamber size to improve overall cardiac output.

BACKGROUND OF INVENTION

It is known that individuals having a sedentary lifestyle, lacking in exercise, have more health problems than active individuals. One result of a sedentary lifestyle is that the size of the heart's main chambers can decrease. This is also occurs as an effect of prolonged hypertension that increases the muscle thickness at the cost of the chamber size. A decrease in cardiac chamber volumes reduces the stroke volume which has implications on the generation of cardiac output by the heart. This limitation in cardiac output greatly reduces the ability to exercise.

Heart failure with preserved ejection fraction (HFpEF) is now the most frequent cause of heart failure. HFpEF is frequently associated with hypertension (HTN), concentric left ventricular hypertrophy (LVH), a reduced LV chamber size and increased left ventricular stiffness. Impaired LV filling and small chamber size reduce the functional capacity through a limitation of cardiac output reserve. There is no rational treatment for HFpEF.

SUMMARY OF THE INVENTION

Presented herein are devices and methods for improving heart function using cardiac pacemakers. In some aspects the invention is an implantable device. The implantable device is a cardiac pacemaker having a sensor for detecting a heart rate, and a processor that is configured to produce an output signal based on detection of a resting heart rate level, the output signal designed to elevate the heart rate over the resting heart rate level. The pacemaker optionally may include various detectors and functionalities. For instance the pacemaker may include a motion or physical activity detector, a position detector, a night function, and/or a remote monitoring device.

The output signal of the device is produced when the resting heart rate is detected. In some embodiments the signal is produced with the resting heart rate is detected for at least 1, 5, 10, 15, or 30 minutes. In other embodiments the resting heart rate is detected for at least one hour before the signal is produced.

The pacemaker in some embodiments comprises a housing, wherein the sensor extends from the housing. The sensor may have an input circuit that receives a signal representative of a heartbeat sensed within a heart as a function of time.

In other aspects, the invention is a method for increasing a heart rate in a subject using a pacemaker when a resting state heart rate is detected. In some embodiments the resting state heart rate is detected for at least 10 minutes or at least 30 minutes. In other embodiments the subject is stimulated to have an increased heart rate for at least 30 minutes.

In some embodiments the subject is not otherwise indicated for a currently accepted treatment with a pacemaker. For instance, the subject may be an obese subject. Alternatively or additionally, the subject may have high blood pressure and/or heart failure with preserved ejection fraction.

In other embodiments the pacemaker includes a motion or physical activity detector and wherein when the pacemaker detects movement or physical activity of the subject, stimulation of the heart rate is reduced or pacing is discontinued.

Kits comprising one or more components of a pacemaker of the present invention are also provided. The kit may optionally include instructions for implanting and or operating the device of the present invention in hard copy or computer readable form.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF THE DRAWINGS

Aspects of the invention are described in connection with the following illustrative non-limiting drawings in which like numerals reference like elements, and wherein:

FIG. 1 depicts a cardiac pacemaker implanted in a body with a wire extending into the heart.

DETAILED DESCRIPTION

Figure 1:
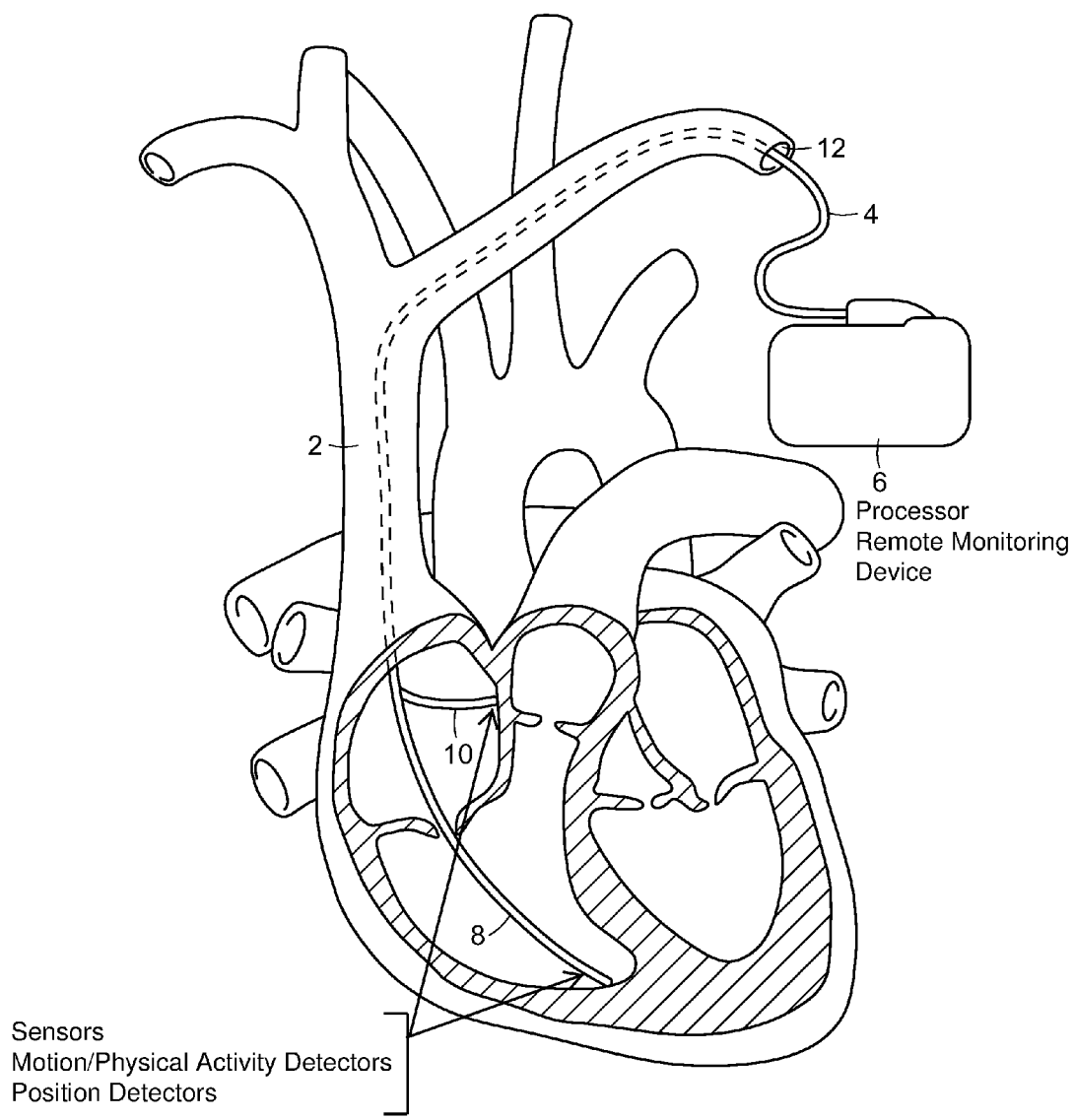
FIG. 1 is a diagram of one embodiment of the inventive device shown in the context of a heart.

An increase in heart rate to above normal resting rates can enlarge the heart. In fact if this heart rate is well above normal rates patients can develop enlarged heart chambers and a clinical phenotype that is commonly called tachycardia induced cardiomyopathy. Endurance athletes such as Tour de France bicycle riders can increase their chamber sizes to levels that are considered to be enlarged. This allows them to increase cardiac output to exceptional levels that allows exercise capacities at supra-physiological levels. Because these changes can regress with inactivity they are considered to be benign and are called athlete's heart. Patients who develop atrial fibrillation with uncontrolled rapid ventricular conduction can develop a similar enlargement of their chamber volumes. If the heart rate is uncontrolled for prolonged times it can result in "tachycardia induced cardiomyopathy". Restoration of the heart rate to normal levels with or without medications can quickly regress the enlargement of the main chambers.

Myocardial tissue has plasticity and is capable of remodeling. Myocardium rapidly adapts to a change in circulatory demands. For instance, hypertension-induced LVH. Heart rate (HR) also affects myocardial remodeling. Increased HRs with endurance exercise and during pregnancy contribute to an LV chamber enlargement of up to twice the normal size. This type of LV remodeling is reversible.

LV chamber expansion without increase in LV mass can also be induced in animals through tachycardia pacing. This phenotype also quickly reverses upon restoration of a normal heart rate. Tachycardia-induced LV chamber enlargement is also seen in patients after atrial fibrillation associated ventricular tachycardia. In this setting it is not known if restoration of normal ventricular rates would be in of itself sufficient to reduce LV chamber size.

The invention in some aspects relates to myocardial pacing-induced LV remodeling. A symptomatic improvement of a patient with HFpEF after atrial fibrillation with rapid ventricular conduction that restored normal LV chamber dimensions and improved diastolic function has been observed. As described in the Examples section, a study designed to analyze the feasibility of pacing-mediated LV remodeling in a porcine model. This proof-of-concept study includes control animals with a normal blood pressure (no HTN) and hypertensive LVH animals (HTN/LVH) induced by unilateral renal artery stenosis (2K1C model) to demonstrate that pacing-mediated LV remodeling can be accomplished in the typical spectrum of normal EF phenotypes. The effect of low and moderate level tachycardia on LV geometry and function will be studied longitudinally to provide insights into the necessary HR requirements. The experimental design will allow for within and between group comparisons. Beneficial effects on diastolic function may be demonstrated in HTN/LVH animals in a 9 week survival study. This time is necessary to develop a phenotype and study the effects of pacing-mediated LV remodeling.

In some aspects the invention involves the use of cardiac pacemakers to normalize chamber volumes in patients with a reduction in heart size and limitations in exercise capacity. Such patients are typically susceptible to heart failure symptoms such as shortness of breath. During resting times such as sleeping the pacemaker is programmed to rates that will stimulate a chamber enlargement, in order to normalize heart size. This approach would also mimic physiological aspects of exercise and therefore condition the heart muscle.

Pacemakers can provide for heart rates observed in atrial fibrillation. According to the invention pacemakers can also provide the same effect in patients with small chamber volumes. The resulting increase in chamber size will allow them to exercise more and reduce symptoms.

Provided herein are methods and devices for performing normalizing heart chamber volumes in a subject. Heart chamber volumes are well known to the skilled artisan. A subject having a small heart chamber volume is one that has a lower than normal cardiac output. Such a subject may be diagnosed as having a small heart chamber volume based on echocardiography or any other cardiac imaging modality, cardiac output, symptoms such as shortness of breath or other means known to the skilled physician.

FIG. 1 illustrates one embodiment of the device in the context of a heart. A pacemaker 6 having a wire 4 extending therefrom is shown. The wire 4 extends through the subclavian vein 12 and past the superior vena cava 2 in the example. The wire optionally splits into a wire to the right atrium 10 and a wire to the right ventricle 8. The sensors or electrodes typically detect electrical activity in the heart and send data through the wires to the computer in the processor. If the heart rhythm is a resting heart rhythm, the computer will direct the processor/generator to send electrical pulses to the heart. The pulses then travel through the wires to reach heart, where the heart is stimulated to increase heart rate.

A cardiac pacemaker as used herein is a self-contained unit that sends electrical stimulation to the heart. Typically a pacemaker is implanted into a subject to alleviate symptoms of decreased cardiac output related to an abnormally low heart rate and/or rhythm. Pacemakers are generally used for persistent, symptomatic second- or third-degree atrioventricular (AV) block and symptomatic sinus and atrial bradycardia. While the methods of the invention may be accomplished using standard pacemakers known in the art, the methods are pacemaker is programmed to perform a different function—that is to increase stimulation of the heart at certain times. Pacemakers have been described in for instance: US2001012954A, U.S. Pat. No. 4,688,573A, U.S. Pat. No. 4,803,987A, U.S. Pat. No. 5,467,773A, U.S. Pat. No. 3,885,552A, U.S. Pat. No. 5,694,940A, U.S. Pat. No. 6,485,416B, U.S. Pat. No. 3,885,552A, U.S. Pat. No. 4,567,892A each of which is incorporated by reference.

A pacemaker may comprise a number of pacemaker components, such as an analog commutator, area amplifier, peak amplitude amplifier, pulse width-hold control circuit, pacer pulse selector, pacer pulse amplifier, ecg amplifier, high speed electro-cardiogram ecg preamplifier, control logic system, VCO audio system. Pacemakers have been described in for instance: US2001012954A, U.S. Pat. No. 4,688,573A, U.S. Pat. No. 4,803,987A, U.S. Pat. No. 5,467,773A, U.S. Pat. No. 3,885,552A, U.S. Pat. No. 5,694,940A, U.S. Pat. No. 6,485,416B, U.S. Pat. No. 3,885,552A, U.S. Pat. No. 4,567,892A each of which is incorporated by reference.

Figure 2:
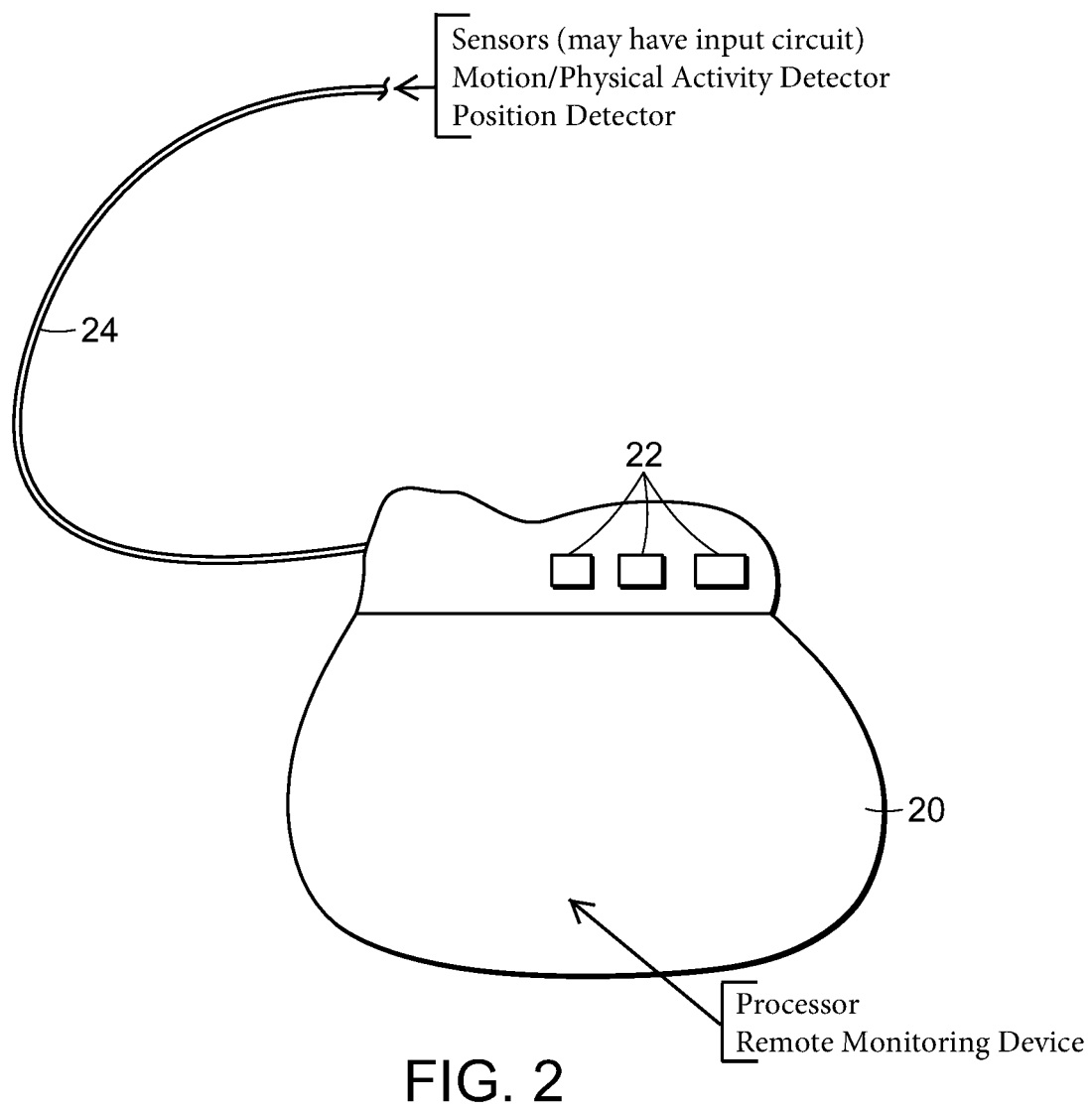
FIG. 2 is one embodiment of the cardiac pacemaker useful according to the invention.

In some embodiments the pacemaker may be a single-chamber pacemaker, in this type, only one pacing lead is placed into a chamber of the heart, either the atrium or the ventricle. In other embodiments the pacemaker may be a dual-chamber pacemaker. Here, wires are placed in two chambers of the heart. One lead paces the atrium and one paces the ventricle. This type more closely resembles the natural pacing of the heart by assisting the heart in coordinating the function between the atria and ventricles. A cardiac pacemaker system typically consists of a battery, a computerized generator or processor, and wires with sensors sometimes referred to as electrodes on one end. The battery and the generator/processor are located in the housing. The battery powers the generator/processor. The wires extend from the housing and connect the generator to the heart. An exemplary cardiac pacemaker is shown in FIG. 2. A sensor in the form of a wire 24 extends from the housing 20. The sensor will be implanted into a subjects heart. The sensor wire can be split such that it interacts with multiple chambers of the heart, or it may simply interact with one chamber. The sensor detects the heart rate and sends a signal to a processor in the pacemaker. Thus, the sensor may have an input circuit that receives a signal representative of a heartbeat sensed within a heart as a function of time. When a resting heart rate is detected on output signal is produced by a processor. The output signal stimulates the heart to increase the heart rate over the resting heart rate level.

The subject may be stimulated to have an increased heart rate for any amount of time. The amount of time that the heart rate is increased may be predetermined. For instance the device may be set to produce an increase in heart rate for at least 5, 10, 15, 30, or 60 minutes or longer. Alternatively the device may include a motion or physical activity detector. Such a detector may be set to stop sending the signal for increased heart rate upon motion or physical activity of the subject. For instance if the subject gets up from rest the motion or physical activity detector would sense movement by the subject and the pacemaker would stop sending the electrical signal that lead to an increased heart activity. A pacemaker may also be programmed with both a time for the increased heart activity and a motion or physical activity detector and the time or the motion of the subject, whichever happens first can signal the pacemaker to reduce the heart rate or shut off the signal. Many pacemakers also had a motion detector that is typically used in subjects who cannot increase the heart rate with exercise. In these prior art devices, the motion detector increases the subjects heart rate in response to activity to correct a pathological inability to increase the heart rate sufficiently with exercise. In contrast, to the instant method as the subject starts to move to pacemaker "kicks in" and provides a high heart rate. This provides the subject with an increased number of heart beats per minute which increases cardiac output and allows them to exercise again.

The pacemaker in some embodiments may be programmed to be responsive to the position or movement of the body. For instance the pacemaker may have sensors that detect changes in the subject's physical activity and automatically adjust the pacing rate to achieve a normal heart rate. For example, if the pacemaker is set to pace at a higher than resting heart rate at night while the subject is asleep, if the sensor detects movement suggesting the subject is awake and moving around the rate will be reduced to a resting level. If the subject stops the movement for a period of time, such as 5 minutes then the pacemaker will be again provide a rate that is higher than the resting rate.

A cardiac pacemaker may also comprise a control device including a position detector connected to a movement sensor, wherein the position detector has a classification device for recognizing short movements. This type of sensor may also be used to detect motion or position that would trigger the pacemaker to operate at a resting rate.

The pacemaker may include a feedback sensor, such that when a low heart rate is detected the rate of the stimulation will be increased. The pacemakers of the invention ideally have such a feature programmed into the software.

The cardiac pacemakers useful according to the invention include any known commercially available cardiac pacemakers. The pacemakers are programmed or set to stimulate an increase in heart rate upon detection of a resting heart rate or at a regular time of rest. Pacemakers include both temporary and permanent pacemakers, both of which are useful according to the invention.

A pacemaker uses low-energy electrical pulses to stimulate the heart and change the rate at which the heart beats. When the pacemaker is used in the method of the invention it causes a slow heart rhythm, referred to as a resting heart rate to speed up. A resting heart rate as used herein refers to a heart rate that is within a range associated with a subject at rest, such as a subject that is asleep. A normal resting heart rate is in the range from 40-90 per minute. The pacemakers described herein are programmed to increase the heart rate to a level greater than a normal resting heart rate. In some embodiments the heart rate is increased to a level with a normal range of an active subject. A normal range of an active heart rate is 90-150/min. In some instances, it may be desirable to raise the heart rate above normal levels. It is sufficient according to the methods of the invention to continuously pace the heart of subjects with small chamber volumes at increased rates. In some embodiments it is desirable for the motion sensor to be integrated into a feedback loop that controls pacing e.g. as the subject is resting or sleeping and no motion is detected the pacemaker would deliver a higher pacing rate.

The pacemakers may also include other known functionalities such as a position detector, a night function, and/or a remote monitoring device. Most contemporary pacemakers have a night function in which a heart rate can be set at a fixed rate. Some pacemakers can also monitor blood temperature, breathing rate, and other factors and adjust your heart rate to these changes.

A night function feature in a pacemaker involves the control of the base rate using at least one sensor that can monitor a physiological parameter. Different phases such as rest phase and resumption of activity phase are detected by the sensor and send a signal to adapt the base rate of the pacemaker accordingly. The base rate is allowed to increase above the normally programmed resting rate or base rate in response to actual patient rest, to encourage a rapid cardiac rhythm to stimulate the heart muscle. Examples of night function mechanisms or settings are disclosed in U.S. Pat. No. 5,645,576A, U.S. Pat. No. 5,861,011A, and U.S. Pat. No. 6,975,903B. Cardiac electrical activity and pacemaker function may be monitored remotely in some instances. For instance medical personnel can remotely monitor the pacing and adjust the pacing levels to increased levels when a patient is at rest. Examples of devices utilizing remote monitoring of vitals or feedback include U.S. Pat. No. 5,919,141A, US2001056229A, US2001023360A, US2002143263A, US2002095093A, US2007282177A, US2006047205A, US2006211934A, US2007027371A, US2008269573A, US2011273309A, and US2006074465A.

Another pacemaker feature is a rate adaptive pacemaker. These devices include a mechanism for determining the demand of the patient, a pacing rate controlling element for controlling the pacing rate in response to the patient's demand, and a pacing rate limiting mechanism for preventing the pacing rate from becoming too low. Patents describing respiration rate and pulmonary sensing and pacemaker feedback include: DE2346223A, U.S. Pat. No. 4,567,892A, U.S. Pat. No. 4,644,954A, U.S. Pat. No. 4,721,110A, U.S. Pat. No. 4,867,161A, EP0242510A, U.S. Pat. No. 4,884,576A, U.S. Pat. No. 5,097,831A, U.S. Pat. No. 5,197,467A, U.S. Pat. No. 5,292,340A, U.S. Pat. No. 5,318,597A, U.S. Pat. No. 5,876,353A, U.S. Pat. No. 4,721,110A, U.S. Pat. No. 4,567,892A, and U.S. Pat. No. 5,876,353A.

The methods of the invention are performed in a subject. A subject, as discussed herein, refers to a human or non-human vertebrate, but is preferably a human. Preferably the human is a patient in need of increasing the cardiac output reserve. For instance, such a patient may have a smaller than normal heart volume. In some instances the subject may already be using a pacemaker or may have other disease indications that call for the use of a pacemaker. In this case the pacemaker can be additionally programmed to perform the methods of the invention.

In other embodiments the subject is not otherwise indicated for a currently accepted treatment with a pacemaker. For instance, the subject may be an obese subject. Alternatively or additionally, the subject may have high blood pressure and/or heart failure with preserved ejection fraction.

A subject typically in need of treatment with a pacemaker is a patient predisposed to developing cardiac problems, such as for instance, a subject having one or more of the following characteristics: Decreased venous blood return, most commonly resulting from reduced blood volume (e.g., hemorrhage) or gravity causing blood to pool in the lower limbs when standing upright; Ventricular diastolic failure (decreased ventricular compliance) caused, for example, by ventricular hypertrophy or impaired relaxation (lusitropy) or Inflow (mitral and tricuspid) valve stenosis, which reduces ventricular filling.

A subject in need of treatment with a pacemaker of the invention, may also include but is not limited to subjects with predispositions to cardiac problems, heart conditions associated with decreasing cardiac chamber sizes and associated heart dysfunction, decreased heart chamber size: Cardiomyopathy, high blood pressure, a subject having an injury or in circumstances where a patient's ability to exercise is impaired. Examples of factors associated with higher risk of cardiovascular disease include but are not limited to HIV, Diabetes, Coronary artery disease, high blood pressure, cardiomyopathy, atherosclerosis, disability, bedridden, air pollution, genetic history or family history of heart failure, high levels of cholesterol, obesity, alcohol, cocaine, smoking or the use of other drugs toxic to the heart (treatment of cancer), autoimmune diseases which have destroyed healthy body tissue and infections involving heart muscles.

Examples of biomarkers which may reflect a higher risk of cardiovascular disease include but are not limited to coronary artery calcification, carotid intima-media thickness, carotid total plaque area, higher fibrinogen and PAI-1 blood concentrations, elevated homocysteine, elevated blood levels of asymmetric dimethylarginine, inflammation as measured by C-reactive protein, elevated blood levels of brain natriuretic peptide (also known as B-type) (BNP).

Other configurations will be easily envisioned by the skilled artisan and are within the scope of the invention.

The present invention is further illustrated by the following Examples, which are not to be construed as limiting the scope of the invention in any manner.

EXAMPLES

Example 1

The effect of low and moderate level tachycardia on LV geometry and function will be studied longitudinally to provide insights into the necessary HR requirements. The experimental design will allow for within and between group comparisons. Beneficial effects on diastolic function may be demonstrated in HTN/LVH animals in a 9 week survival study. This study will involve the development of a phenotype and the study of the effects of pacing-mediated LV remodeling.

A total of 4 age-matched female Yucatan micro pigs (9 month) will be studied in a 1×4 month longitudinal duplicate study.

One group will be animals with normal blood pressure (no HTN animals). These animals will be treated by the following protocol:

Day 1: Pacemaker implantation, sensing only to establish average heart rate
3 weeks: Baseline Echocardiogram, Blood Pressure
PPM: permanent A(V) pacing rate=1.5×average heart rate
5 weeks: Echocardiogram, Blood Pressure
PPM: permanent A(V) pacing rate=2×average heart rate
7 weeks: Echocardiogram, Blood Pressure
PPM off: sensing only
9 weeks: Echocardiogram, Blood Pressure, LV weight
Data processing and interim Analysis A second group or treatment animals—hypertensive LVH animals (HTN/LVH animals) will be treated as follows:

Day 1: Pacemaker implantation, sensing only to establish average heart rate
Unilateral renal artery stenosis (metal coil, fluoroscopic >80% stenosis)
[MAP increase ~30 mmHg, LV mass increase ~20%]
3 weeks: Baseline Echocardiogram, Blood Pressure
PPM: permanent A(V) pacing rate=1.5×average heart rate
5 weeks: Echocardiogram, Blood Pressure
PPM: permanent A(V) pacing rate=2×average heart rate
7 weeks: Echocardiogram, Blood Pressure
PPM off: sensing only
9 weeks: Echocardiogram, Blood Pressure, LV weight
Data processing and final analysis Echocardiogram: The animals will be sedated and intubated. Pacing will be suspended and blood pressure will be assessed. A transthoracic and transesophageal echocardiogram will be performed.

Parameters: Septal and posterior wall thickness, average LV wall thickness, end-diastolic and endsystolic LV diameter, modified Simpson's calculation to evaluate LV end-diastolic and end-systolic volume (primary outcome), Devereux equation to estimate LV mass. Left atrial volume will be assessed by the area-length method. Mitral inflow and lateral mitral annulus tissue Doppler to assess diastolic function. LV systolic function (ejection fraction, stroke volume and cardiac output) will be calculated from LV volumes.

Each of the foregoing patents, patent applications and references is hereby incorporated by reference.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, e.g., elements that are conjunctively present in some cases and disjunctively present in other cases. Multiple elements listed with "and/or" should be construed in the same fashion, e.g., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (e.g. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

It should also be understood that, unless clearly indicated to the contrary, in any methods claimed herein that include more than one step or act, the order of the steps or acts of the method is not necessarily limited to the order in which the steps or acts of the method are recited.

I claim:

1. A cardiac pacemaker for implantation within a subject, the pacemaker comprising:
    a housing;
    at least one motion sensor configured to detect movement of the subject and produce output indicative of the movement; and
    at least one processor in the housing, the at least one processor being responsive to the output from the sensor and configured to produce a pacing signal when the output from the at least one motion sensor indicates the subject is at rest, the pacing signal being configured to increase a heart rate of the subject above a resting heart rate level, wherein the pacing signal is configured to stimulate remodeling of the subject's heart muscle.

2. The cardiac pacemaker of claim 1, wherein the at least one processor is further configured to stop producing the pacing signal when the output from the at least one sensor indicates the subject is active.

3. The cardiac pacemaker of claim 1, wherein the at least one processor determines that the subject is at rest by detecting a lack of movement of the subject for a first period of time.

4. The cardiac pacemaker of claim 3, wherein the first period of time is 5 minutes.

5. The cardiac pacemaker of claim 1, further including an input circuit that receives a signal representative of a heartbeat sensed within a heart as a function of time.

6. The cardiac pacemaker of claim 1, wherein the pacing signal is configured to increase the heart rate of the subject to a heart rate between 90 beats per minute and 150 beats per minute.

7. The cardiac pacemaker of claim 1, wherein the at least one processor is further configured to adjust the pacing signal over time based on the output from the at least one motion sensor.

8. The cardiac pacemaker of claim 7, wherein adjusting the pacing signal over time comprises:
    producing a first pacing signal configured to increase the heart rate of the subject to a first heart rate above the resting heart rate level;
    detecting output from the at least one motion sensor that indicates the subject has remained at rest; and
    in response to said detecting, producing a second pacing signal configured to increase the heart rate of the subject to a second heart rate above the resting heart rate level, the second heart rate being higher than the first heart rate.

9. The cardiac pacemaker of claim 1, wherein the output from the at least one motion sensor indicates the subject is sleeping.

* * * * *